(12) United States Patent
Melanson

(10) Patent No.: US 12,365,013 B2
(45) Date of Patent: Jul. 22, 2025

(54) ELECTROSTATIC QUADCOPTER SANITATION DEVICE AND DELIVERY SYSTEM

(71) Applicant: Aeras, LLC, Wexford, PA (US)

(72) Inventor: Justin Melanson, Wexford, PA (US)

(73) Assignee: Aeras, LLC, Wexford, PA (US)

( * ) Notice: Subject to any disclaimer, the term of this patent is extended or adjusted under 35 U.S.C. 154(b) by 839 days.

(21) Appl. No.: 17/245,068

(22) Filed: Apr. 30, 2021

(65

(51) Int. Cl.
  *B64D 1/18* (2006.01)
  *B64U 10/13* (2023.01)
  *B64U 101/29* (2023.01)
  *B64U 30/12* (2023.01)
  *B64U 30/293* (2023.01)
  *B64U 60/50* (2023.01)

(52) U.S. Cl.
  CPC ............ *B64U 30/12* (2023.01); *B64U 30/293* (2023.01); *B64U 60/50* (2023.01); *B64U 2101/29* (2023.01)

(58) Field of Classification Search
  CPC ...... B64U 60/50; B64U 2101/29; B64U 1/18; B64U 30/293; B64U 30/12; B64U 10/13; B08B 6/00
  See application file for complete search history.

(56) References Cited

U.S. PATENT DOCUMENTS

| | | | |
|---|---|---|---|
| 7,913,938 B2 | 3/2011 | Cooper | |
| 9,474,816 B2 | 10/2016 | Park et al. | |
| 9,739,574 B1* | 8/2017 | Vijay | ...................... F41H 11/18 |
| 10,189,971 B2 | 1/2019 | Lima et al. | |
| 10,618,652 B2 | 4/2020 | Tamkin, Sr. | |
| 2010/0096181 A1 | 4/2010 | Nakamura et al. | |
| 2015/0166831 A1* | 6/2015 | Kuehneweg | ............ C08G 18/73 428/423.1 |
| 2015/0264845 A1* | 9/2015 | Bimanand | ............ C09D 175/06 428/408 |
| 2017/0340176 A1 | 11/2017 | Liao | |
| 2019/0071172 A1* | 3/2019 | Caldwell | ................. B64C 27/52 |
| 2019/0168875 A1 | 6/2019 | Ashur et al. | |
| 2020/0091803 A1* | 3/2020 | Richardson | .......... H02K 17/165 |
| 2020/0113166 A1 | 4/2020 | Warren, Jr. et al. | |

FOREIGN PATENT DOCUMENTS

| | | | |
|---|---|---|---|
| CN | 107244417 A | 10/2017 | |
| KR | 10-2014-0060901 A | 5/2014 | |
| KR | 10-1662255 B1 | 10/2016 | |
| WO | WO-2018076471 A1 * | 5/2018 | ............... B64C 1/06 |
| WO | 2019075176 A2 | 4/2019 | |
| WO | 2019130317 A1 | 7/2019 | |
| WO | 2019189929 A1 | 10/2019 | |
| WO | 2020140027 A1 | 7/2020 | |

* cited by examiner

ELECTROSTATIC QUADCOPTER SANITATION DEVICE AND DELIVERY SYSTEM

CROSS-REFERENCE TO RELATED APPLICATIONS

This application claims priority to U.S. Provisional Patent Application Ser. No. 63/018,705, titled "Electrostatic Quadcopter Sanitation Device and Delivery System" and filed on May 1, 2020, the disclosure of which is hereby incorporated by reference in its entirety.

BACKGROUND OF THE INVENTION

Field of the Invention

The invention relates to a system for delivering electrostatically charged particles for sanitation by way of a drone and a manner of electromagnetic shielding for said drone.

Description of Related Art

Electrostatics have been known since classical physics. Materials, such as amber, attract lightweight particles after rubbing. The Greek word for amber, ηλεκτρον, or electron, was thus the source of the word 'electricity'. Electrostatic phenomena arise from the forces that electric charges exert on each other. Such forces are described by Coulomb's law. Coulomb's law states that: The magnitude of the electrostatic force of attraction or repulsion between two point charges is directly proportional to the product of the magnitudes of charges and inversely proportional to the square of the distance between them.

There are many examples of electrostatic phenomena, from those as simple as the attraction of the plastic wrap to one's hand after it is removed from a package, to the apparently spontaneous explosion of grain silos, the damage of electronic components during manufacturing, and photocopier & laser printer operation. Electrostatics involves the buildup of charge on the surface of objects due to contact with other surfaces. Although charge exchange happens whenever any two surfaces contact and separate, the effects of charge exchange are usually only noticed when at least one of the surfaces has a high resistance to electrical flow. This is because the charges that transfer are trapped there for a time long enough for their effects to be observed. These charges then remain on the object until they either bleed off to ground or are quickly neutralized by a discharge: e.g., the familiar phenomenon of a static "shock" is caused by the neutralization of charge built up in the body from contact with insulated surfaces.

When it comes to cleaning surfaces and objects, traditional dry and wet dusting tends to be the first methods that come to mind. While these cleaning techniques are tried and true, they do little more than spread filth around, unless the rags used are washed regularly. Dry dusting kicks up resting particles, redistributing them into the air and onto other surfaces. Wet dusting can involve harmful cleaning chemicals and make it hard to reach certain spots or objects. For sensitive places, like clean rooms, R&D labs, healthcare facility cleaning, and schools, there is a more effective method for stripping dirt, dust, and germs from surfaces that require specialized sanitation: electrostatic spray.

However, as a result of the COVID-19 pandemic, a need for ways to clean surfaces and objects in order to prevent infectious diseases is required. In particular, there exists a need in the art for more efficient and effective cleaning utilizing the benefits of electrostatic properties that can quickly disinfect large-scale venues, reaching up to 100 times more surface area than what is currently known in the art.

By using state of the art electrostatic sprayers, however, the functionality of other devices may suffer. Electrostatic sprayers may emit high frequency or high volume electromagnetic radiation which can interfere with nearby electronic components either on or near the electrostatic sprayer. Thus, there also exists a need to protect electronic equipment near the electrostatic sprayers so that their functionality can be preserved.

SUMMARY OF THE INVENTION

In one non-limiting embodiment or aspect of the present disclosure, an electrostatic cleaning device may include: a flying portion including a body; at least one power source mounted to the body; at least one extension extending from the body defining a hollow interior; at least one propeller configured to generate lift for the electrostatic cleaning device, the at least one propeller being located at an end of the at least one extension opposing the body; and at least one electrical connection extending through the hollow interior, the at least one electrical connection connecting the at least one power source to the propeller; and a spray system including a tank attachably mounted to the flying portion and configured to store a cleaning spray; at least one spray mechanism in fluid communication with the tank and configured to discharge the cleaning spray; and at least one electrostatic generating unit configured to apply a voltage across a spray path of the cleaning spray so that, when the cleaning spray is discharged from the spray system, the cleaning spray is electrostatically charged. At least a portion of the at least one extension may be coated in nanotube particles configured to shield the at least one electrical connection from electromagnetic waves produced by the at least one electrostatic generating unit In one non-limiting embodiment or aspect, the electrostatic cleaning device may include at least two extensions with at least one propeller at the ends thereof. The electrostatic cleaning device may include at least one support mechanism extending between the at least two extensions, and the at least one spray mechanism and the at least one electrostatic generating unit may be supported from the at least one support mechanism. The electrostatic cleaning device may include four extensions with at least one propeller at the ends thereof; a first support mechanism extending between a first pair of extensions; and a second support mechanism extending between a second pair of extensions. A first spray mechanism and a first electrostatic generating unit may be supported from the first support mechanism, and a second spray mechanism and a second electrostatic generating unit may be supported from the second support mechanism. The at least one support mechanism may include a first clip configured to attach to a first extension; a second clip configured to attach to a second extension; and at least one support beam extending between the first clip and the second clip. The at least one support beam may be configured to support the at least one spray mechanism and the at least one electrostatic generating unit therefrom.

In one non-limiting embodiment or aspect, a surface of the hollow interior may be coated in nanotube particles. An outer surface of the at least one extension may be coated in nanotube particles. The at least one power source may be a battery, and a surface of the battery opposing the body may be coated in nanotube particles. The body may include a plurality of legs extending below the at least one extension and configured to support the electrostatic cleaning device. The plurality of legs may include at least one connecting portion extending between a pair of the plurality of legs, the at least one connecting portion configured to support the electrostatic cleaning device.

In another non-limiting embodiment or aspect of the present disclosure, an electrostatic cleaning device may include: a flying portion including a body; and at least one extension extending from the body and configured to generate lift for the electrostatic cleaning device; and a spray system including: a tank attachably mounted to the flying portion and configured to store a cleaning spray; at least one spray mechanism in fluid communication with the tank and configured to discharge the cleaning spray; and at least one electrostatic generating unit configured to apply a voltage across a spray path of the cleaning spray so that, when the cleaning spray is discharged from the spray system, the cleaning spray is electrostatically charged; and a plurality of electromagnetic shields configured to block at least a portion of the electromagnetic waves produced by the electrostatic cleaning device. At least one first electromagnetic shield may extend from at least a portion of the body of the flying portion, and at least one second electromagnetic shield may extend about the at least one electrostatic generating unit.

In a non-limiting embodiment or aspect, the body may include a plurality of legs extending below the at least one extension and configured to support the electrostatic cleaning device. The at least one first electromagnetic shield may extend from at least one of the plurality of legs. The at least one spray mechanism may include at least one nozzle for discharging the cleaning spray. The at least one electrostatic generating unit may be configured to apply a voltage across a spray path of the cleaning spray as it discharges from the nozzle. The at least one second electromagnetic shield may extend about the at least one nozzle and the at least one electrostatic generating unit. The at least one second magnetic shield may extend in at least a partially conical or frustoconical shape about the at least one nozzle and the at least one electrostatic generating unit. The at least one first electromagnetic shield may extend from each of the plurality of legs.

In another non-limiting embodiment or aspect of the present disclosure, an electrostatic cleaning device may include a flying portion; a spray system mounted to the flying portion and including at least one electrostatic generating unit configured to apply a voltage across a spray path of a cleaning spray so that, when the cleaning spray is discharged from the spray system, the cleaning spray is electrostatically charged; and shielding elements provided on at least a portion of the flying portion or a portion of the spray system to shield electronic components of the flying portion from electromagnetic waves produced by the at least one electrostatic generating unit. The shielding elements may be coated about at least a portion of the flying portion. The shielding elements may be shields extending from at least a portion of the flying portion or the spray system. The flying portion may include a quadcopter drone. The shielding elements may include carbon nanotubes.

In some non-limiting embodiments or aspects, the present disclosure may be characterized by one or more of the following numbered clauses:

Clause 1. An electrostatic cleaning device comprising: a flying portion comprising: a body; at least one power source mounted to the body; at least one extension extending from the body defining a hollow interior; at least one propeller configured to generate lift for the electrostatic cleaning device, the at least one propeller being located at an end of the at least one extension opposing the body; and at least one electrical connection extending through the hollow interior, the at least one electrical connection connecting the at least one power source to the propeller; and a spray system comprising: a tank attachably mounted to the flying portion and configured to store a cleaning spray; at least one spray mechanism in fluid communication with the tank and configured to discharge the cleaning spray; and at least one electrostatic generating unit configured to apply a voltage across a spray path of the cleaning spray so that, when the cleaning spray is discharged from the spray system, the cleaning spray is electrostatically charged, wherein at least a portion of the at least one extension is coated in nanotube particles configured to shield the at least one electrical connection from electromagnetic waves produced by the at least one electrostatic generating unit.

Clause 2. The electrostatic cleaning device of clause 1, comprising at least two extensions with at least one propeller at the ends thereof.

Clause 3. The electrostatic cleaning device of clause 1 or 2, comprising at least one support mechanism extending between the at least two extensions, wherein the at least one spray mechanism and the at least one electrostatic generating unit are supported from the at least one support mechanism.

Clause 4. The electrostatic cleaning device of any of clauses 1-3, comprising four extensions with at least one propeller at the ends thereof; a first support mechanism extending between a first pair of extensions; and a second support mechanism extending between a second pair of extensions, wherein a first spray mechanism and a first electrostatic generating unit are supported from the first support mechanism, and a second spray mechanism and a second electrostatic generating unit are supported from the second support mechanism.

Clause 5. The electrostatic cleaning device of any of clauses 1-4, wherein the at least one support mechanism comprises a first clip configured to attach to a first extension; a second clip configured to attach to a second extension; and at least one support beam extending between the first clip and the second clip, the at least one support beam configured to support the at least one spray mechanism and the at least one electrostatic generating unit therefrom.

Clause 6. The electrostatic cleaning device of any of clauses 1-5, wherein a surface of the hollow interior is coated in nanotube particles.

Clause 7. The electrostatic cleaning device of any of clauses 1-6, wherein an outer surface of the at least one extension is coated in nanotube particles.

Clause 8. The electrostatic cleaning device of any of clauses 1-7, wherein the at least one power source is a battery, and a surface of the battery opposing the body is coated in nanotube particles.

Clause 9. The electrostatic cleaning device of any of clauses 1-8, wherein the body comprises a plurality of legs extending below the at least one extension and configured to support the electrostatic cleaning device.

Clause 10. The electrostatic cleaning device of any of clauses 1-9, wherein the plurality of legs includes at least one connecting portion extending between a pair of the plurality of legs, the at least one connecting portion configured to support the electrostatic cleaning device.

Clause 11. An electrostatic cleaning device comprising: a flying portion comprising: a body; at least one extension extending from the body and configured to generate lift for the electrostatic cleaning device; and a spray system comprising: a tank attachably mounted to the flying portion and configured to store a cleaning spray; at least one spray mechanism in fluid communication with the tank and configured to discharge the cleaning spray; and at least one electrostatic generating unit configured to apply a voltage across a spray path of the cleaning spray so that, when the cleaning spray is discharged from the spray system, the cleaning spray is electrostatically charged; and a plurality of electromagnetic shields configured to block at least a portion of the electromagnetic waves produced by the electrostatic cleaning device, wherein at least one first electromagnetic shield extends from at least a portion of the body of the flying portion, and at least one second electromagnetic shield extends about the at least one electrostatic generating unit.

Clause 12. The electrostatic cleaning device of clause 11, wherein the body comprises a plurality of legs extending below the at least one extension, the plurality of legs configured to support the electrostatic cleaning device, and wherein the at least one first electromagnetic shield extends from at least one of the plurality of legs.

Clause 13. The electrostatic cleaning device of clause 11 or 12, wherein the at least one spray mechanism includes at least one nozzle for discharging the cleaning spray, wherein the at least one electrostatic generating unit is configured to apply a voltage across a spray path of the cleaning spray as it discharges from the nozzle, and wherein the at least one second electromagnetic shield extends about the at least one nozzle and the at least one electrostatic generating unit.

Clause 14. The electrostatic cleaning device of any of clauses 11-13, wherein the at least one second magnetic shield extends in a partially conical or frustoconical shape about the at least one nozzle and the at least one electrostatic generating unit.

Clause 15. The electrostatic cleaning device of any of clauses 11-14, wherein the at least one first electromagnetic shield extends from each of the plurality of legs.

Clause 16. An electrostatic cleaning device comprising: a flying portion; a spray system mounted to the flying portion and comprising at least one electrostatic generating unit configured to apply a voltage across a spray path of a cleaning spray so that, when the cleaning spray is discharged from the spray system, the cleaning spray is electrostatically charged; and shielding elements provided on at least a portion of the flying portion or a portion of the spray system to shield electronic components of the flying portion from electromagnetic waves produced by the at least one electrostatic generating unit.

Clause 17. The electrostatic cleaning device of clause 16, wherein the shielding elements are coated about at least a portion of the flying portion.

Clause 18. The electrostatic cleaning device of clause 16 or 17, wherein the shielding elements are shields extending from at least a portion of the flying portion or the spray system.

Clause 19. The electrostatic cleaning device of any of clauses 16-18, wherein the flying portion comprises a quadcopter drone.

Clause 20. The electrostatic cleaning device of any of clauses 16-19, wherein the shielding elements comprise carbon nanotubes.

BRIEF DESCRIPTION OF THE DRAWINGS

FIG. 1 is a perspective view of an electrostatic cleaning device according to one embodiment or aspect of the present disclosure;

FIG. 2 is a top view of the electrostatic cleaning device of FIG. 1;

FIG. 3 is a partially exploded perspective view of a tank of the electrostatic cleaning device of FIG. 1;

FIG. 4 is a partially exploded perspective view of the electrostatic cleaning device of FIG. 1;

FIG. 5A is a perspective view of a hose attachment process of the electrostatic cleaning device of FIG. 1;

FIG. 5B is a perspective view of a hose attachment process of the electrostatic cleaning device of FIG. 1;

FIG. 6. is a perspective view of a clamp according to one aspect or embodiment of the present disclosure;

FIG. 7 is an exploded view of an electrostatic generating device, a spray nozzle, and supports of the electrostatic cleaning device of FIG. 1;

FIG. 8A is a cross-sectional view of an extension of the electrostatic cleaning device of FIG. 1 according to one aspect or embodiment of the present disclosure taken along line A-A in FIG. 2;

FIG. 8B is a cross-sectional view of an extension of the electrostatic cleaning device of FIG. 1 according to one aspect or embodiment of the present disclosure taken along line A-A in FIG. 2;

FIG. 9 is a diagram of the nanotube shield according to one aspect or embodiment of the present disclosure;

FIG. 10 is a perspective view of an electrostatic generating device and spray nozzle according to another aspect or embodiment of the present disclosure; and FIG. 11 is a perspective view of another electrostatic cleaning device according to one embodiment or aspect of the present disclosure.

DETAILED DESCRIPTION OF THE INVENTION

As used herein, the singular forms of "a", "an", and "the" include plural referents unless the context clearly dictates otherwise.

Spatial or directional terms, such as "left", "right", "inner", "outer", "above", "below", and the like relate to the disclosure as shown in the drawing figures and are not to be considered as limiting, as the disclosure can assume various alternative orientations.

All numbers and ranges used in the specification and claims are to be understood as being modified in all instances by the term "about". By "about" is meant plus or minus twenty-five percent of the stated value, such as plus or minus ten percent of the stated value. However, this should not be considered as limiting to any analysis of the values under the doctrine of equivalents.

Unless otherwise indicated, all ranges or ratios disclosed herein are to be understood to encompass the beginning and ending values and any and all subranges or subratios subsumed therein. For example, a stated range or ratio of "1 to 10" should be considered to include any and all subranges or subratios between (and inclusive of) the minimum value of 1 and the maximum value of 10; that is, all subranges or subratios beginning with a minimum value of 1 or more and ending with a maximum value of 10 or less. The ranges and/or ratios disclosed herein represent the average values over the specified range and/or ratio.

The terms "first", "second", and the like are not intended to refer to any particular order or chronology, but refer to different conditions, properties, or elements.

The term "at least" is synonymous with "greater than or equal to".

The term "not greater than" is synonymous with "less than or equal to".

As used herein, "at least one of" is synonymous with "one or more of". For example, the phrase "at least one of A, B, and C" means any one of A, B, or C, or any combination of any two or more of A, B, or C. For example, "at least one of A, B, and C" includes one or more of A alone; or one or more B alone; or one or more of C alone; or one or more of A and one or more of B; or one or more of A and one or more of C; or one or more of B and one or more of C; or one or more of all of A, B, and C.

The term "includes" is synonymous with "comprises".

As used herein, the terms "perpendicular" or "substantially perpendicular" mean a relative angle as between two objects at their real or theoretical intersection is from 85° to 90°, or from 87° to 90°, or from 88° to 90°, or from 89° to 90°, or from 89.5° to 90°, or from 89.75° to 90°, or from 89.9° to 90°, inclusive of the recited values.

With reference to FIGS. 1, 2, 4, and 11, an electrostatic cleaning system 10 according to the present application is shown. In a first non-limiting embodiment, shown in FIGS. 1, 2, and 4, the electrostatic cleaning system 10 includes a flying portion 12 and a spray system 14. As shown, the flying portion 12 is a quadcopter drone, and the term "drone" may be used interchangeably with flying portion 12. It is contemplated that other flying devices, such as different drones, or remote-control helicopters may be used within the cleaning system 10. The functions and methods of the cleaning system 10 may apply to remotely controlled flying devices or to flying devices that require a pilot. In short, the electrostatic cleaning system 10 operates by having the drone 12 fly the spray system 14 around an area, so that electrostatically charged cleaning particles can be applied to various surfaces in order to clean the surfaces.

The drone 12 includes a body 20 which acts as a central hub for the drone 12 and the electrostatic cleaning system 10 more generally. Within or attached to the body 20 is a power source 30, such as a battery. The power source 30 will provide power to the elements that require it in order to get the electrostatic cleaning system 10 to fly. The body 20 may also include various controllers, processors, sensors, and other electronics housed therein, and these devices may serve to operate and control the drone 12. Examples of such electronics include radar 11, a GPS tracking system, and a display panel for providing visual information to a user of the drone 12 when not in flight.

Figure 4:
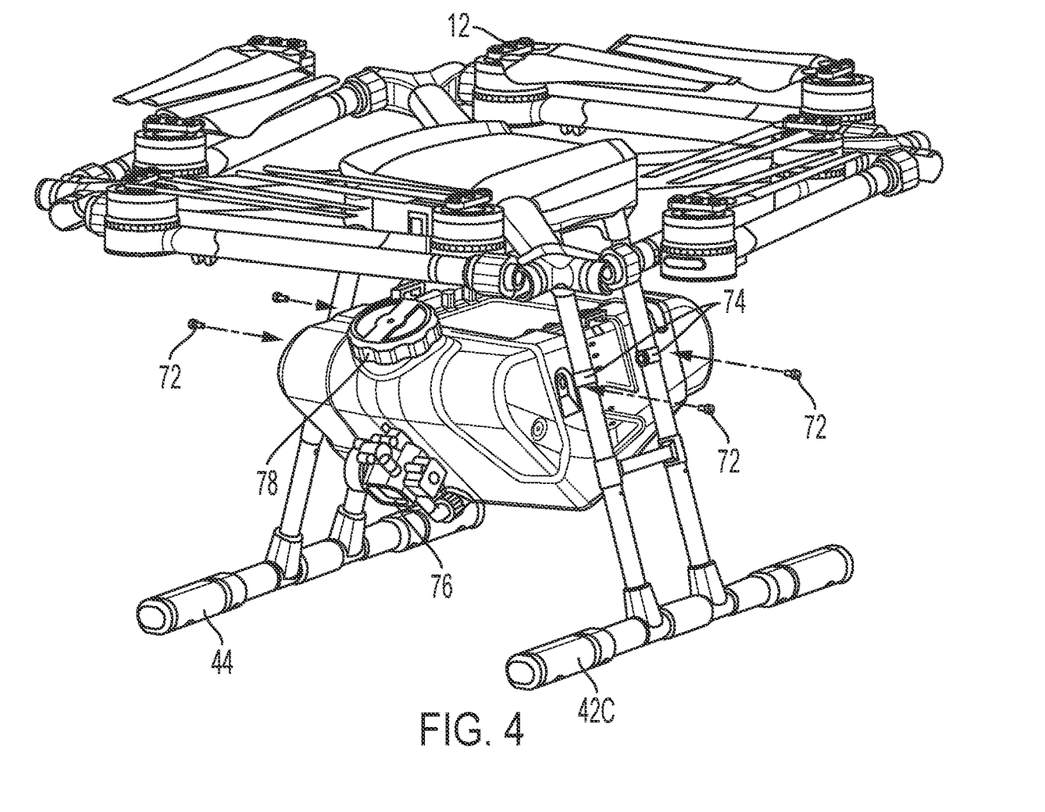
Figure 5A:
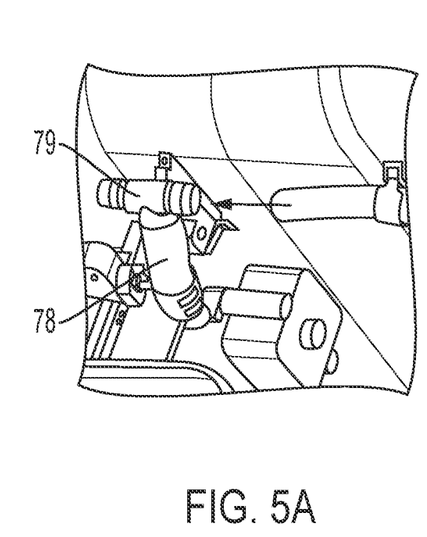
Figure 5B:
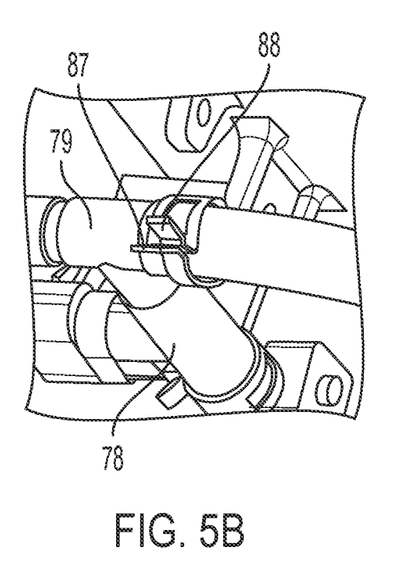

Wings 22, 24, 26, 28 extend from the body 20. As shown, four wings 22, 24, 26, 28 extend from the body 20, although any number of wings may be used as long as the wings and their associated features can provide enough lift and velocity for the electrostatic cleaning system 10 to fly. Each wing 22, 24, 26, 28 includes two branches 22a, 22b, 24a, 24b, 26a, 26b, 28a, 28b. At the end of each branch 22a, 22b, 24a, 24b, 26a, 26b, 28a, 28b is a rotary blade 32a, 32b, 34a, 34b, 36a, 36b, 38a, 38b. Each rotary blade 32a, 32b, 34a, 34b, 36a, 36b, 38a, 38b is designed to be powered to provide the lift and velocity to fly the electrostatic cleaning system 10. Although rotary blades are shown, other flying elements known to those having ordinary skill in the art may be used. As shown in FIG. 4, the branches 22a, 22b, 24a, 24b, 26a, 26b, 28a, 28b can fold inwardly so that the electrostatic cleaning system can have a smaller footprint for storage purposes.

Figure 8A:
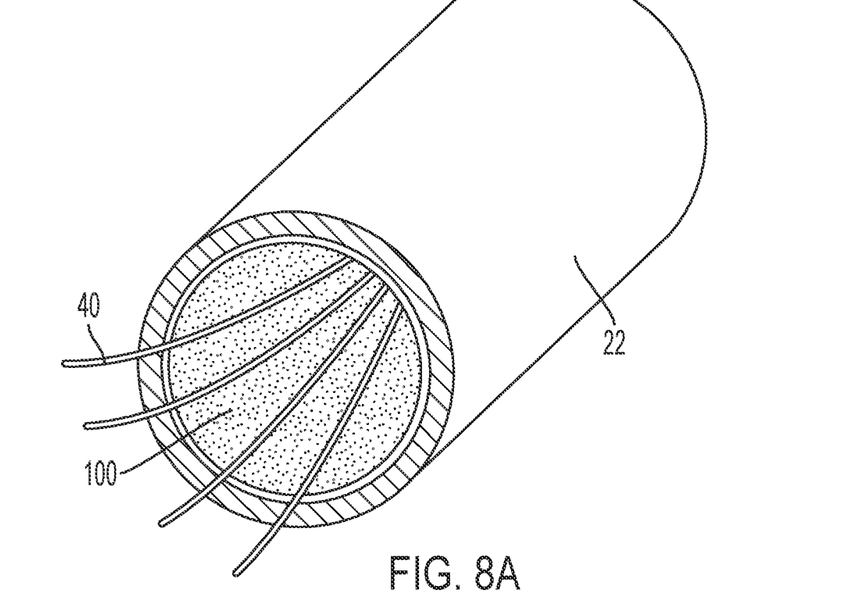
Figure 8B:
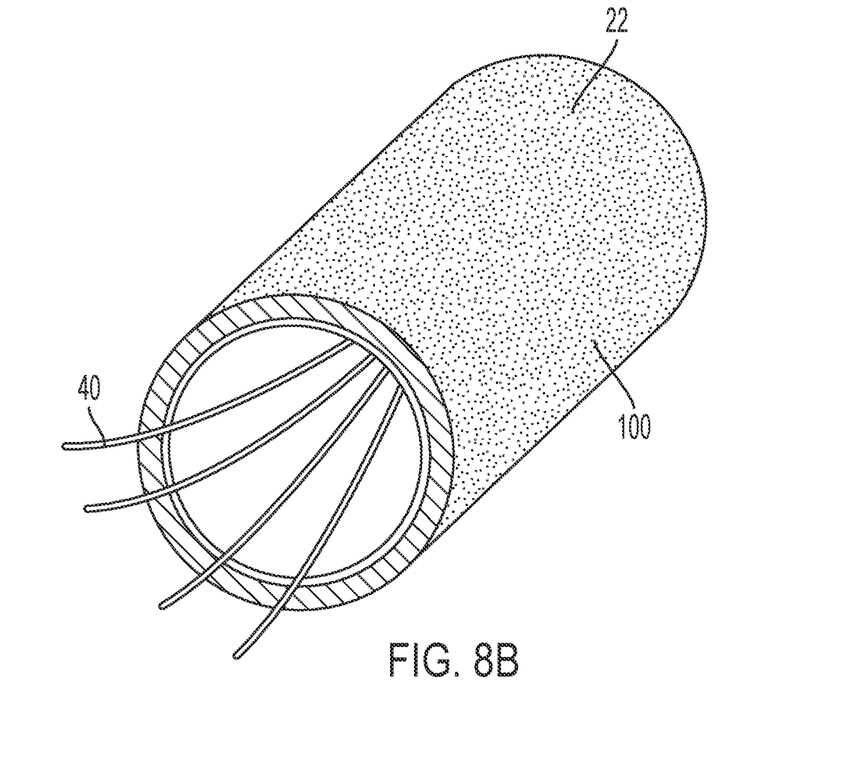
Figure 9:
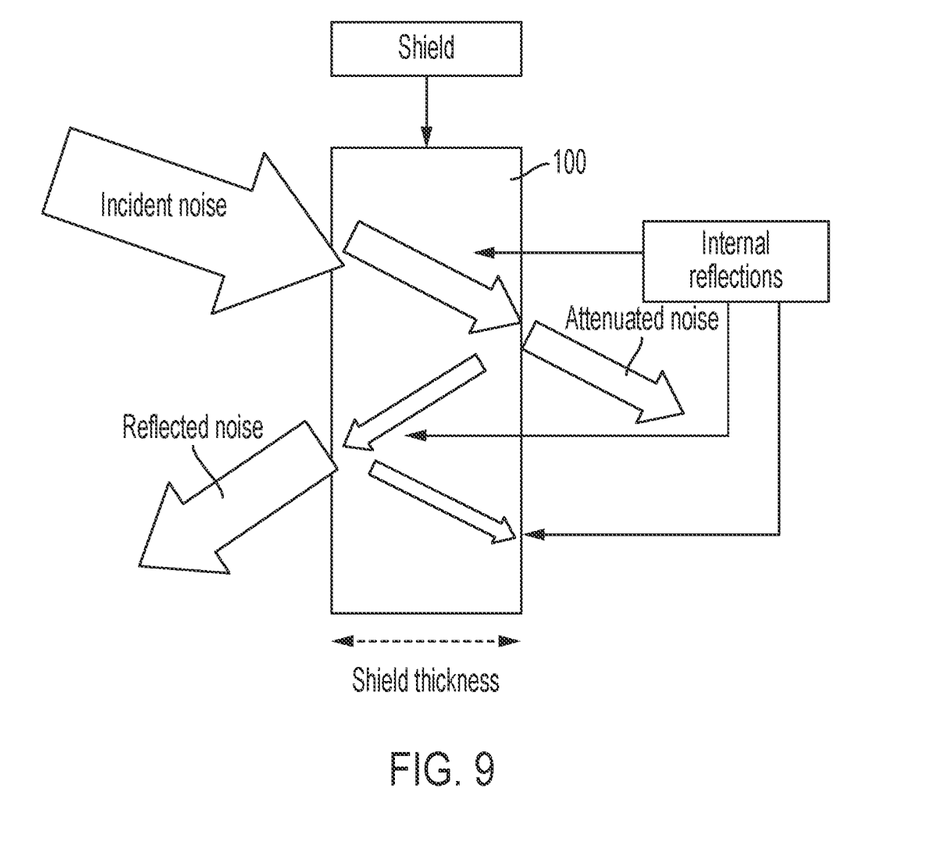
Figure 10:
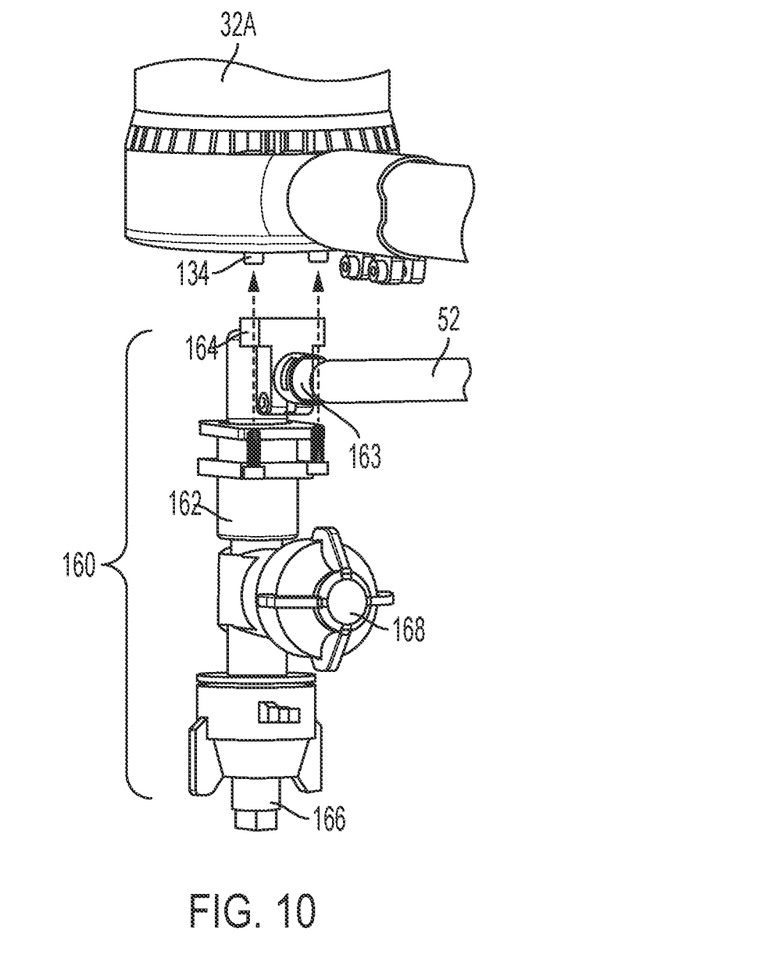
Figure 11:
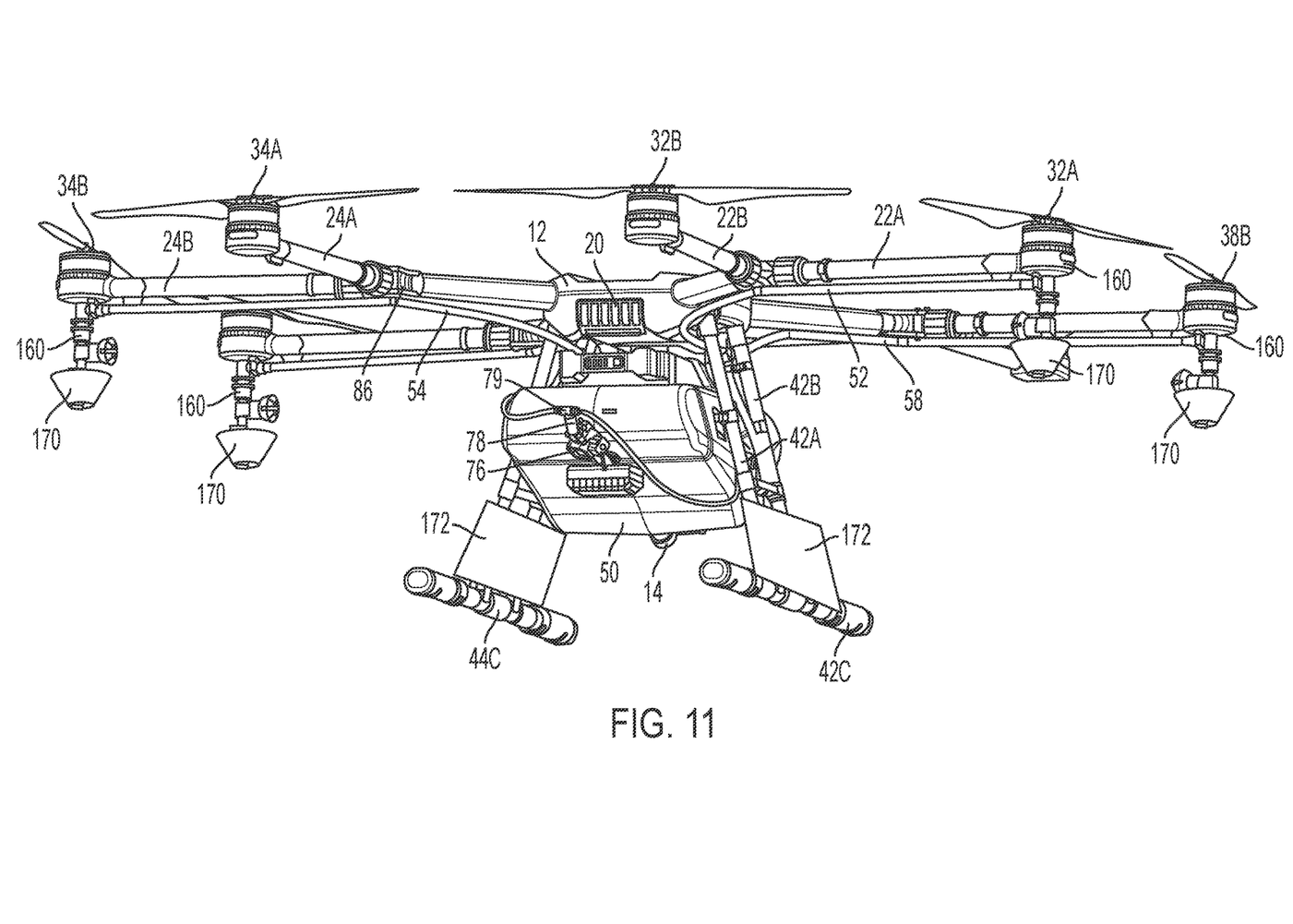

In order to power the rotary blades 32a, 32b, 34a, 34b, 36a, 36b, 38a, 38b, electrical connections 40, shown in FIGS. 8A and 8B, extend from the power source 30 to the rotary blades 32a, 32b, 34a, 34b, 36a, 36b, 38a, 38b. The electrical connections 40 extend through hollow interiors defined by the wings 22, 24, 26, 28 and branches 22a, 22b, 24a, 24b, 26a, 26b, 28a, 28b in order to connect to the rotary blades 32a, 32b, 34a, 34b, 36a, 36b, 38a, 38b.

Extending from the body 20 in a downward direction, generally perpendicular to the wings 22, 24, 26, 28, are legs 42, 44, which provide a surface for the electrostatic cleaning system 10 to rest upon when not in use. As shown, each leg 42, 44 includes two vertical legs 42a, 42b, 44a, 44b, extending downwardly and one horizontal leg 42c, 44c extending across the ends of and connecting the two vertical legs 42a, 42b, 44a, 44b. The two vertical legs 42a, 44a, 42b, 44b may be welded to or molded with the horizontal legs 42c, 44c. Other connection methods known to those having skill in the art may also be used. A band (not numbered) may also wrap around the vertical legs 42a, 44a, 42b, 44b so as to prevent bowing and to keep their lengths aligned relative to one another as the legs 42, 44 experience the stresses associated with landing. The vertical legs 42a, 42b, 44a, 44b may be slightly angled relative to the orthogonal made with the ground so that the horizontal legs 42c, 44c may provide the most efficient support for the electrostatic flying system 10.

Figure 3:
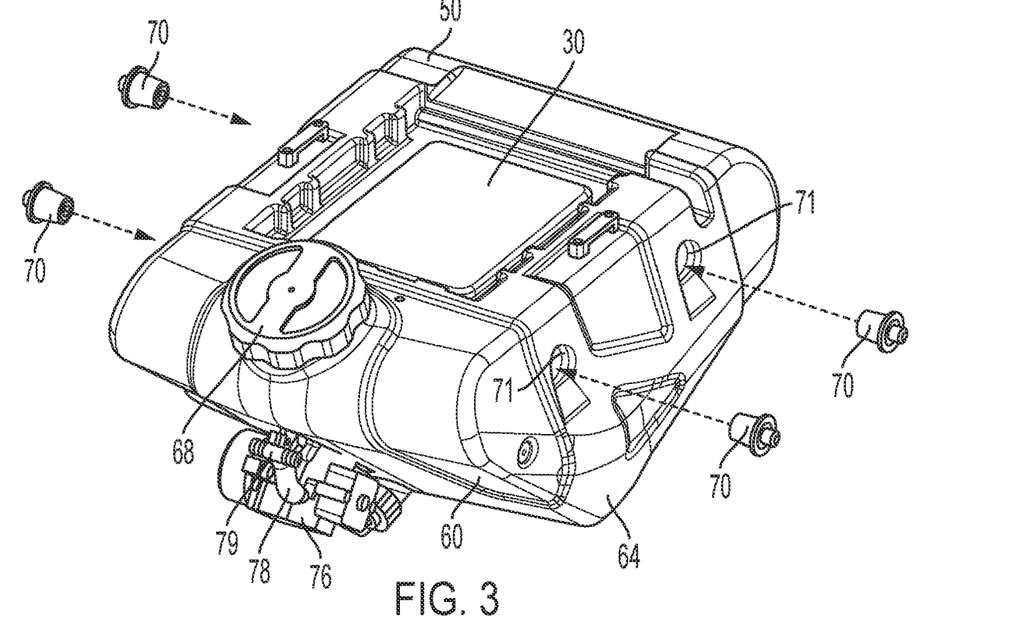

With reference to FIGS. 1-7 the spray system 14 includes a tank 50 for holding a cleaning solution, tubes 52, 54, 56, 58, extending from the tank 50 and electrostatic sprayers 60 connected to the tubes 52, 54, 56, 58. The tank 50 defines an internal volume 66 for holding a cleaning solution that will ultimately be forced out of the electrostatic cleaning system 10 by way of the electrostatic sprayers 60. As shown in FIGS. 3 and 4, the tank 50 includes a body 64 for defining the internal volume 66, a cap 68, and plugs 70. The cap 68 is located on a side of the tank 50 so that when the tank 50 is attached to the drone 12, a user can remove the cap 68 and fill the internal volume 66 with cleaning solutions, such as electrostatic cleaning solutions approved by the Environmental Protection Agency. Both the tank 50 and the cap 68 are made of plastic, although other materials are contemplated. The plugs 70 are received by corresponding holes 71 in the sides of the tank body 64. The plugs 70 are made of rubber or another flexible material and allow the tank body 64 to flex and bend during flight, thus helping to prevent failure of the tank 50 as a result of rapid movement with a tank volume 66 full of cleaning solution.

The tank 50 is attached to the drone 12 between the legs 42, 44. The tank 50 includes holes 71 that align with an attachment piece 72 for receiving fasteners 74 therethrough. The attachment pieces 72 wrap around the vertical legs 42a, 42b, 44a, 44b so that, by fastening the fasteners 74 through the attachment pieces 72 and holes 71, the tank 50 will be secured between the legs 42, 44 of the drone 12. Fasteners such as zip ties, welding, snap fits, and others known in the art may be used as well.

Figure 6:
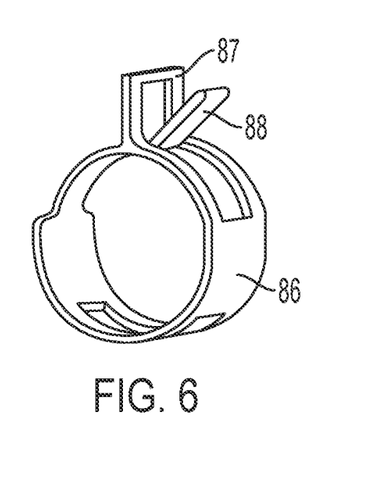

A pump 76 is mounted to the tank 50 to pump the cleaning solution through the tubes 52, 54, 56, 58 and out the electrostatic sprayers 60. The pump 76 may be powered by the battery 30 located on the body 20 of the drone 12, or it may have another power source. As shown in FIGS. 1 and 3-5B, the pump 76 draws the cleaning solution from the tank 50 and out of a lead tube 78. The lead tube 78 connects to a T-fitting 79 which connects to two of the four tubes 52, 54. The tubes 52, 54, are inserted into the opposing ends of the T-fitting 79 and connected to those ends by way of hose clips 86, one of which is shown in FIG. 6. The hose clips 86 are generally cylindrical and include a first tab 87 defining an opening through which a second tab 88 can fit. The friction between the tabs 87, 88 retains them in place and the hose clip 86 is clamped around the ends of the T-fitting 79 and tubes 52, 54. The hose clips 86 also connect and secure each tube 52, 54, 56, 58 to free parts of the drone 12.

Figure 1:
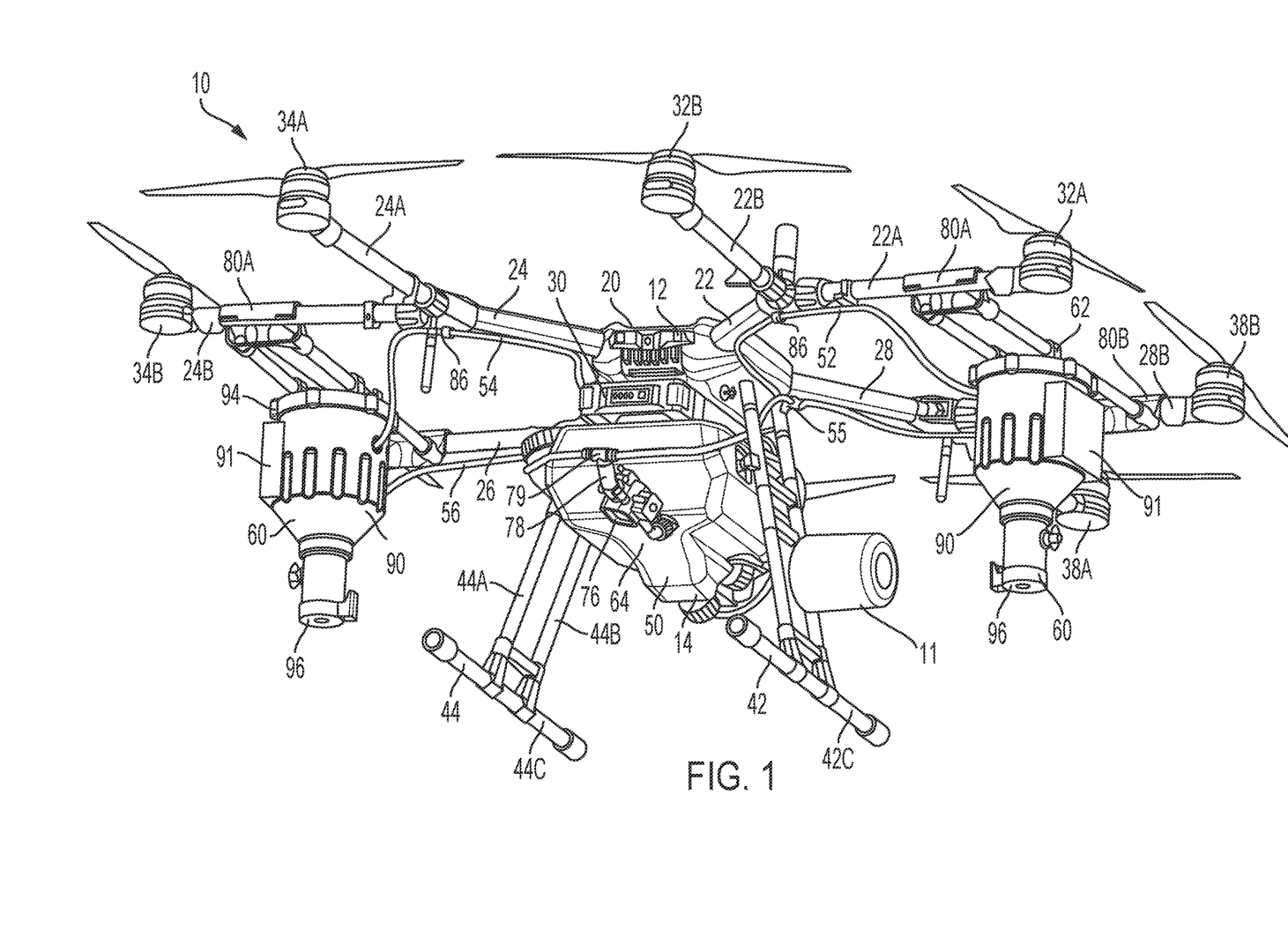
Figure 2:
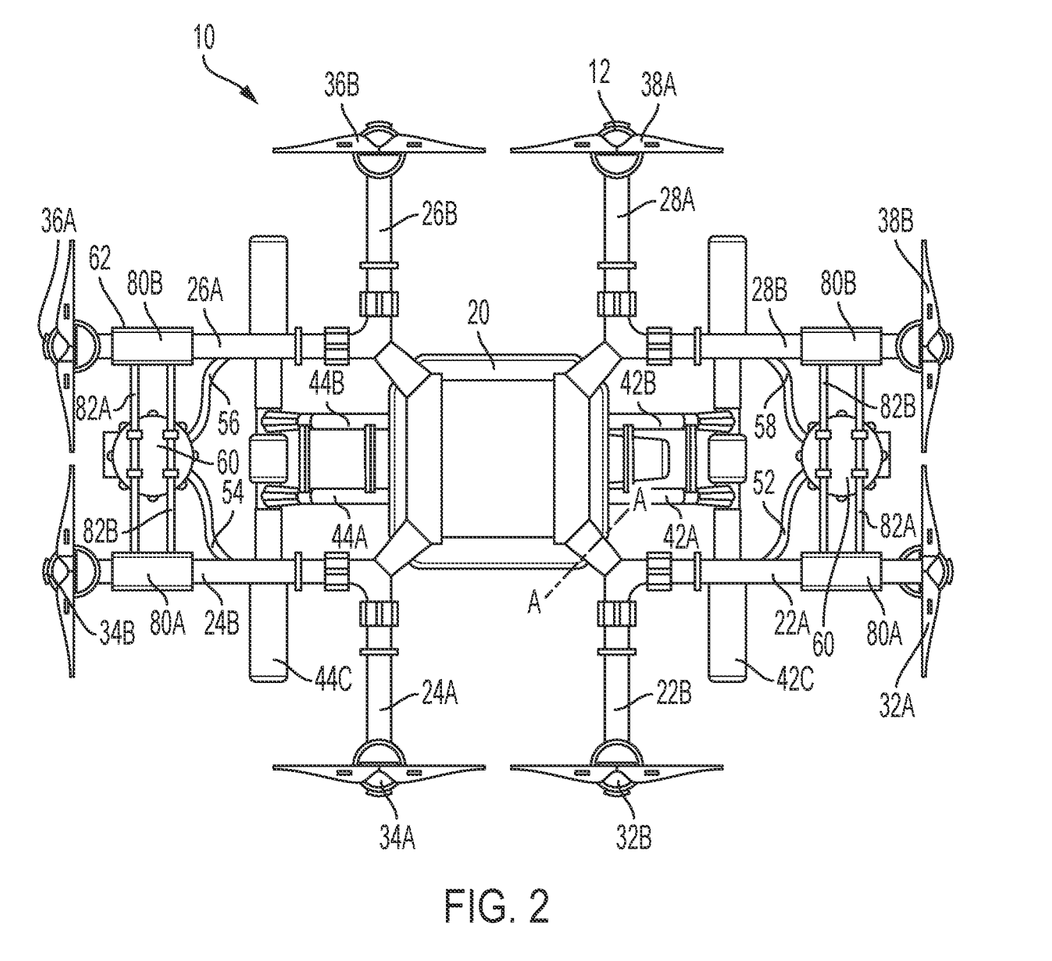

From the tubes 52, 54, the cleaning solution is pumped to branching points 55, as shown in FIG. 1, where some of the cleaning solution enters into the remaining tubes 56, 58 while some remains in tubes 52, 54. From there, the cleaning solution is pumped through the electrostatic sprayers 60 and out of the system 10. While only one branching point 55 is visible in FIG. 1, a second branching point is located at a symmetrical location on the side of the drone opposite the side having branching point 55.

As shown in FIGS. 1, 2, 7, and 10, the electrostatic sprayers 60 include a body 90, defining a hole 92 for receiving the tubes 52, 54, 56, 58 so that the cleaning solution can enter the electrostatic sprayers 60. The electrostatic sprayers 60 also include a cap 94, a nozzle 96, and a knob 98. Within the body 90 is an electrostatic generating device 91. The electrostatic generating device 91 creates a charge by way of an electrode that atomizes the cleaning solution as it travels through the sprayer 60. The generating device 91 may be approximately 2.5 inches by 3.5 inches by 1 inch in volume and may apply 80,000 kilovolts to the disinfectant in order to apply a charge, typically positive, to the cleaning solution. This charge causes the solution to attach to oppositely charged items across a cleaning surface or area over which the solution is sprayed. This means that the cleaning solution, upon exiting the nozzle 96, will repel itself and spread out across a cleaning surface leading to a more efficient cleaning while eliminating the waste and overuse of the chemicals. In other words, surfaces already covered with the cleaning solution will repel nearby spray particles. This action causes the cleaning solution to expand across the cleaning area. As more of the area is covered in the cleaning solution, the individual particles of the solution will travel to uncovered areas as a result of the repulsions created by similarly charged cleaning solution particles.

Figure 7:
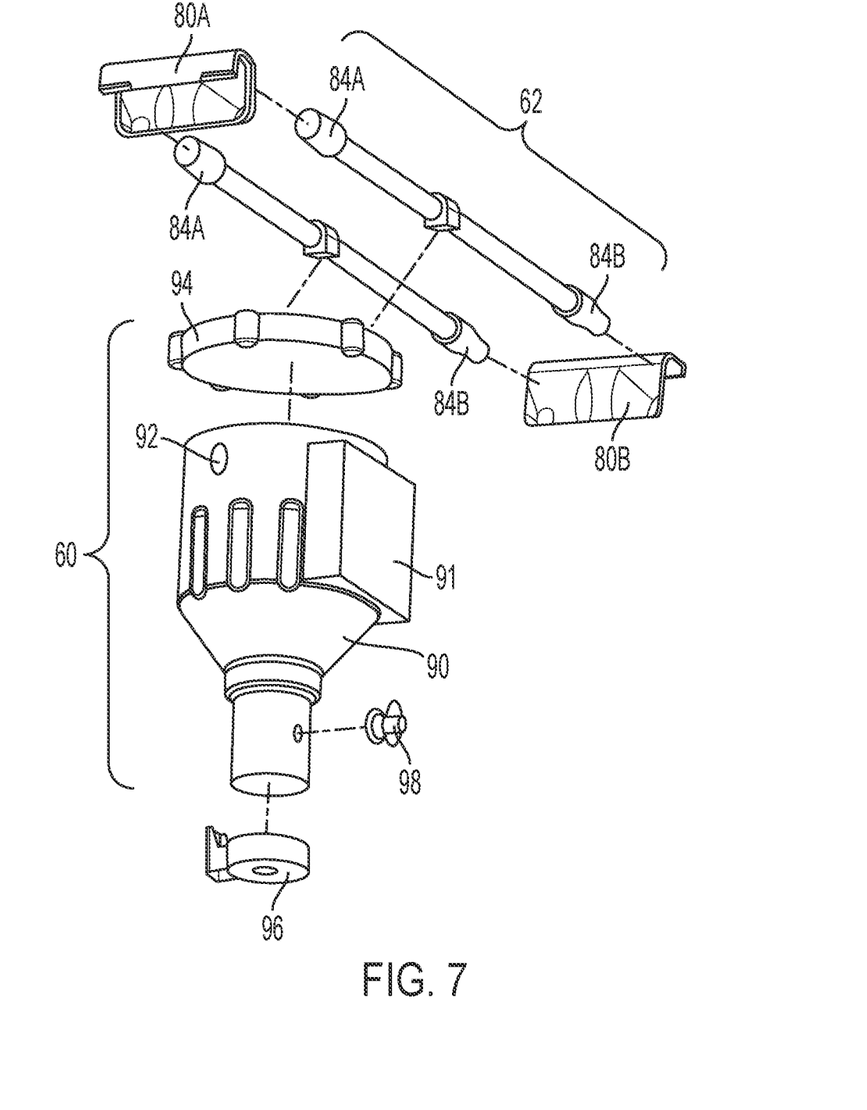

In order to be applied to a cleaning area or a cleaning surface, the cleaning solution passes through a nozzle 96 after interacting with the electrostatic generating device 91 within the body 90. The nozzle 96 can be a nozzle known to those having skill in the art. For example, the nozzle 96 can include a 24 volt pump that pumps the cleaning solution towards an outlet of the nozzle 96 where the cleaning solution is then atomized by high pressure air provided within the nozzle 96 prior to being jettisoned from the nozzle 96. The nozzle 96 sprays the now-charged cleaning solution over the to-be-disinfected surface area. A knob 98 on the nozzle 96 can adjust the nozzle 96 so that the stream or spray of the cleaning solution takes the desired form depending on the specific application of the electrostatic cleaning system 10. The cap 94, located above the body 90 of the electrostatic sprayer 60, connects the electrostatic sprayer 60 to the electrostatic cleaning system 10.

In particular, the top of the cap 94 may be welded, glued, molded to, or tied to (using hose clips 86) supports 62. A corresponding pair of clips may also be applied, one extending between the supports 62 and the other extending from the top of the cap 94 in the direction of the supports 62 may also be used. The supports 62 extend across two branches 22b, 28a. The supports 62 include wing clips 80a, 80b that extend over the branches 22b, 28a and form a friction fit with each other in order to secure the supports 62 in place. The wing clips 80a, 80b include bushings 82a, 82b extending in a generally perpendicular direction to the branches 22b, 28a. The bushings 82a, 82b receive the ends of extensions 84a, 84b therein. The extensions 84a, 84b can be screwed into the bushings 82a, 82b, snap fit into the bushings 82a, 82b, or connected to the bushings 82a, 82b via a friction fit. The electrostatic sprayer 60 can attach to the extensions 84a, 84b at approximately a midpoint between the branches 22b, 28a. The supports 62 can be made of plastic or another resilient material to keep the electrostatic sprayers 60 secured between the branches 22b, 28a during normal operation of the drone 12. As shown, two supports 62 extend across two branches 24b, 26a, but it is understood that any number of supports 62 can extend between any two adjacent branches 22a, 22b, 24a, 24b, 26a, 26b, 28a, 28b. Additional electrostatic sprayers 60 can extend from the supports 62 in accordance with this disclosure as well.

During operation of the electrostatic cleaning system 10, the electrostatic sprayer 60 and, in particular, the electrostatic generating unit creates a high electrostatic charge. This charge creates electromagnetic waves that can interfere with other electronic devices, such as the battery 30, to rotary blade 32a, 32b, 34a, 34b, 36a, 36b, 38a, 38 connection and operation. Other electronic devices in the body 20 of the drone 12 may also experience interference or inoperability during operation of the electrostatic sprayers 60. In a worst-case scenario, this interference can lead to the drone 12 failing to operate mid-flight, resulting in a crash. In other cases, the drone 12 may become unresponsive to commands input by a user previously controlling the drone via remote. The drone 12 may also begin taking inaccurate flight paths as a result of these issues. In order to prevent the electronics of the electrostatic cleaning system 10 from experiencing this, the other electronic components can be protected by shielding components 100, 170, 172.

Specifically, electromagnetic interferences (EMIs) occur when electromagnetic signals are unintentionally transmitted from one element to another by radiation and/or conduction, such as the EMIs generated by the electrostatic generating unit. High-frequency signals can be conducted through and along power wires used throughout the drone 12. Thus the shielding components 100, 170, 172 must either attenuate the electromagnetic radiation created or neutralize the electromagnetic radiation that falls in the gigahertz range. Attenuation occurs by damping the electromagnetic radiation and/or EMIs so that the magnitude and overall quality of the radiation is such that it can no longer interfere with electrical components. Neutralization of the electromagnetic radiation can either occur by blocking or absorbing the radiation to prevent it from reaching critical electronic components.

The actual application of the shielding components 100, 170, 172 will be discussed below. Each shielding component 100, 170, 172 is designed to ultimately prevent electrons from being conducted through the drone and reaching various electronic components as a result of the electromagnetic charges and EMIs created by the electrostatic sprayers 60. One way in which this can be done is by mixing multiwall carbon nanotubes (MWCNTS) with a silver paste to either coat a device to be protected from the electromagnetic charge, as is the case with coatings 100, or to form a shield to be applied around the to-be-protected electronic components or around the sources of the electromagnetic charges, as is the case with shields 170, 172. Graphite may also be used, either as a layer applied to the mixture of the MWCNTS and silver paste or as an additional component of the MWCNTS-silver paste. Graphite helps to reflect the undesirable radiation that falls within the gigahertz range.

As seen in FIGS. 8A and 8B, the wings 22, 24, 26, 28 may either be internally or externally coated with the MWCNT silver paste mixture as discussed above. This protective coating 100, for example, can be applied around the wings 22, 24, 26, 28. This coating 100 may be placed on the interior or the exterior surfaces of the wings 22, 24, 26, 28 to provide the same result: protecting the electrical current running from the battery 30 and through the wires 40 from being interfered with during operation of the electrostatic sprayers 60. Although only the wings 22, 24, 26, 28, are shown as being coated, it is understood that other parts of the drone 12 housing electronic elements such as the body 20 and branches 22*a*, 22*b*, 24*a*, 24*b*, 26*a*, 26*b*, 28*a*, 28*b* may also have this coating. The inside or outside of the electro-static static sprayer 60 may also receive a layer of the protective coating 100, preventing any damaging EMIs from escaping the main source of the electromagnetic radiation.

FIG. 9 is an exemplary diagram of what happens as a result of the coating 100 being applied to the wings 22, 24, 26, 28. The coating 100 causes the incoming incident noise to be either reflected immediately backwards or reflected within the coating 100. These internal reflections ensure that only attenuated noise, which does not affect electronic equipment, can pass through the coating 100. In other words, the coating 100 attenuates, neutralizes, and reflects electro-magnetic radiation which in turn prevents interference from occurring as a result of the radiation.

Referring now to FIGS. 10 and 11, another embodiment of an electrostatic sprayer 160 for an electrostatic cleaning system 10 with nanotube shielding is shown. In this embodiment, the electrostatic sprayers 160 are attached directly under the rotary blades 32*a*, 32*b*, 34*a*, 34*b*, 36*a*, 36*b*, 38*a*, 38*b*. As shown in FIG. 10, t4 electrostatic sprayers 160 also include a body 162 with a hole 163 for a tube 52, 54, 56, 58 and an electrostatic generating unit located inside. The sprayers 160 also include a nozzle 166 for spraying the electrically charged cleaning solution and a knob 168 for adjusting the spray of the nozzle 166. The electrostatic sprayer 160 also includes a clip 164 that snap fits into a corresponding receptor 134 located on the drone 12 under the rotary blades 32*a*, 32*b*, 34*a*, 34*b*, 36*a*, 36*b*, 38*a*, 38*b*. Other attachment methods described herein or known to those having skill in the art may also be used.

In order to protect the electrical equipment from the electromagnetic charges, shields 170, 172 may be placed around the part of the electrostatic sprayer 160 that includes the electrostatic generating unit and be extended from the horizontal legs 40*c*, 42*c*. The shields 170 are wrapped around the electrostatic generating units within the body 162 of the electrostatic sprayers 160. The shields 170 take a conical or frustoconical shape so that the drone 12 is shielded from the electromagnetic radiation generated by the electrostatic sprayers 160. The cone shields 170 still permit the charged cleaning solution to be dispersed from the nozzle 166 by having a hole located at the exit point of the cleaning solution or by having an entire opening in the shield 170 be present on the side of the shield 170 opposite the drone 12. Shields 172 are rectangular shaped and extend upwardly, in the direction of the drone body 20, from the horizontal legs 40*c* 42*c*. This protects the electronics located at or near the tank 50 from failing as a result of electro-magnetic radiation. It is understood that a mix of the two embodiments described herein can be used. For example, the wings 22, 24, 26, 28 may be coated in nanotube particles while one or both of the shields 170, 172 just described may be placed around the drone.

While specific embodiments of the device of the present disclosure have been described in detail, it will be appreciated by those skilled in the art that various modifications and alternatives to those details could be developed in light of the overall teachings of the disclosure. Accordingly, the particular arrangements disclosed are meant to be illustrative only and not limiting as to the scope of the device of the present disclosure, which is to be given the full breadth of the claims appended and any and all equivalents thereof.

What is claimed is:

1. An electrostatic spraying device comprising:

a flying portion comprising:

a body;

at least one extension extending from the body and configured to generate lift for the electrostatic spraying device;

electronics configured to operate the flying portion; and a pair of horizontal legs extending along sides of the body, the pair of horizontal legs being configured to support the flying portion on a surface;

a spray system comprising:

a tank attachably mounted to the flying portion and configured to store a fluid;

at least one spray mechanism in fluid communication with the tank and configured to discharge the fluid; and at least one electrostatic generating unit configured to apply a voltage across a spray path of the fluid so that, when the fluid is discharged from the spray system, the fluid is electrostatically charged; and a plurality of shields configured to block at least a portion of the electromagnetic waves produced by the electrostatic spraying device, wherein the at least one spray mechanism and the at least one electrostatic generating unit extend from the at least one extension, wherein at least one first shield of the plurality of shields extends from at least one of the pair of horizontal legs, such that the electronics are protected from the at least a portion of the electromagnetic waves.

2. The electrostatic spraying device of claim 1, wherein the at least one spray mechanism includes at least one nozzle for discharging the fluid, wherein the at least one electrostatic generating unit is configured to apply a voltage across a spray path of the fluid as it discharges from the nozzle, and wherein at least one second shield of the plurality of shielding elements extends about the at least one nozzle and the at least one electrostatic generating unit, such that the electronics are protected from the at least a portion of the electromagnetic waves.

3. The electrostatic spraying device of claim 2, wherein the at least one second shield extends radially about the at least one nozzle and the at least one electrostatic generating unit.

4. The electrostatic spraying device of claim 1, wherein the at least one first-shielding element shield extends from both of the horizontal legs.

5. An electrostatic spraying device comprising:

a flying portion comprising a body and a plurality of wings configured to generate lift for the electrostatic spraying device;

a spray system mounted to the flying portion and comprising at least one electrostatic generating unit configured to apply a voltage across a spray path of a fluid so that, when the fluid is discharged from the spray system, the fluid is electrostatically charged; and shields provided on at least a portion of the flying portion or a portion of the spray system to shield electronic components of the flying portion from electromagnetic waves produced by the at least one electrostatic generating unit, wherein the electrostatic generating unit extends from at least one wing of the plurality of wings, and wherein the shields comprise at least one first shield extending around the electrostatic generating unit.

6. The electrostatic spraying device of claim 5, further comprising a shielding coating, and wherein the plurality of wings are coated with the shielding coating.

7. The electrostatic spraying device of claim 5, wherein the flying portion comprises a pair of landing legs configured to support the flying portion on a surface, wherein the shields comprise at least one second shield, and wherein the at least one second shield extends from at least one of the pair of landing legs.

8. The electrostatic spraying device of claim 5, wherein the flying portion comprises a quadcopter drone.

9. The electrostatic spraying device of claim 5, wherein the shields comprise carbon nanotubes.

10. The electrostatic spraying device of claim 3, wherein the at least one first shield and the at least one second shield comprise carbon nanotubes.

11. The electrostatic spraying device of claim 6, wherein the plurality of wings are configured to hold electrical connections extending from the flying portion to a plurality of rotary blades corresponding to the plurality of wings.

12. An electrostatic spraying device comprising:
a flying portion comprising:
a body;
at least one extension extending from the body and configured to generate lift for the electrostatic spraying device; and
electronics configured to operate the flying portion;
a spray system comprising:
a tank attachably mounted to the flying portion and configured to store a fluid;
at least one spray mechanism in fluid communication with the tank and configured to discharge the fluid; and
at least one electrostatic generating unit configured to apply a voltage across a spray path of the fluid so that, when the fluid is discharged from the spray system, the fluid is electrostatically charged; and a plurality of shields configured to block at least a portion of the electromagnetic waves produced by the electrostatic spraying device, wherein the at least one spray mechanism and the at least one electrostatic generating unit extend from the end of the at least one extension, wherein the plurality of shields comprise at least one shielding cone, the at least one shielding cone extends about the at least one spray mechanism and the at least one electrostatic generating unit, such that the electronics are protected from the at least a portion of electromagnetic waves.

13. The electrostatic spraying device of claim 12, wherein the at least one shielding cone extends radially about the at least one spray mechanism and the at least one electrostatic generating unit.

14. The electrostatic spraying device of claim 13, wherein the at least one shielding cone extends in at least a partially conical or frustoconical shape about the at least one electrostatic generating unit.

15. The electrostatic spraying device of claim 12, wherein the body comprises a plurality of legs extending below the at least one extension, and wherein the plurality of shields comprise at least one shielding plate, the at least one shielding plate extending from at least one of the plurality of legs.

16. The electrostatic spraying device of claim 15, wherein the plurality of legs comprises a pair of horizontal legs extending along sides of the body and configured to support the flying portion on a surface, and wherein the at least one shielding plate extends from at least one of the pair of horizontal legs.

17. The electrostatic spraying device of claim 16, wherein the at least one shielding plate extends from both of the horizontal legs.

18. The electrostatic spraying device of claim 1, wherein the plurality of shielding elements comprise a coating that is coated on the at least one extension.

19. The electrostatic spraying device of claim 18, wherein the at least one extension comprises a plurality of extensions each of the plurality of extensions having a rotary blade to generate the lift for the electrostatic spraying device.

20. The electrostatic spraying device of claim 19, wherein the plurality of extensions are configured to hold electrical connections extending from the electronics to the rotary blades.

* * * * *

UNITED STATES PATENT AND TRADEMARK OFFICE
CERTIFICATE OF CORRECTION

| | | |
|---|---|---|
| PATENT NO. | : 12,365,013 B2 | Page 1 of 1 |
| APPLICATION NO. | : 17/245068 | |
| DATED | : July 22, 2025 | |
| INVENTOR(S) | : Justin Melanson | |

It is certified that error appears in the above-identified patent and that said Letters Patent is hereby corrected as shown below:

In the Claims

Column 12, Line 55, Claim 4, delete "first-shielding element shield" and insert -- first shield --

Column 13, Line 8, Claim 6, delete "claim 5," and insert -- claim 5 --

Signed and Sealed this
Sixteenth Day of September, 2025

Coke Morgan Stewart
*Acting Director of the United States Patent and Trademark Office*